(12) United States Patent
Peterson et al.

(10) Patent No.: US 7,815,682 B1
(45) Date of Patent: Oct. 19, 2010

(54) SPINAL FUSION IMPLANT AND RELATED METHODS

(75) Inventors: Mark Peterson, Central Point, OR (US); Matthew Curran, Carlsbad, CA (US)

(73) Assignee: NuVasive, Inc., San Diego, CA (US)

( * ) Notice: Subject to any disclaimer, the term of this patent is extended or adjusted under 35 U.S.C. 154(b) by 292 days.

(21) Appl. No.: 11/525,674

(22) Filed: Sep. 22, 2006

Related U.S. Application Data

(60) Provisional application No. 60/719,845, filed on Sep. 24, 2005.

(51) Int. Cl.
*A61F 2/44* (2006.01)
(52) U.S. Cl. .................................................. 623/17.16
(58) Field of Classification Search ............... 623/17.11, 623/17.12–17.15, 17.16
See application file for complete search history.

(56) References Cited

U.S. PATENT DOCUMENTS

| 5,782,919 | A * | 7/1998 | Zdeblick et al. | 623/17.16 |
| 5,888,227 | A * | 3/1999 | Cottle | 623/17.16 |
| 6,974,480 | B2 * | 12/2005 | Messerli et al. | 623/17.16 |
| 2002/0082683 | A1 * | 6/2002 | Stinson et al. | 623/1.23 |
| 2003/0139813 | A1 * | 7/2003 | Messerli et al. | 623/17.11 |
| 2005/0096745 | A1 * | 5/2005 | Andre et al. | 623/17.11 |

* cited by examiner

*Primary Examiner*—Eduardo C Robert
*Assistant Examiner*—Steven J Cotroneo
(74) *Attorney, Agent, or Firm*—Jonathan Spangler

(57) ABSTRACT

A spinal fusion implant of non-bone construction for introduction into any variety of spinal target sites. The implant may include generally arcuate anterior and posterior sides. The implant may also include a wedged shaped distal end which can provide self-distraction of vertebral endplates during insertion and positioning of the spinal fusion implant.

44 Claims, 7 Drawing Sheets

SECTION A-A

SPINAL FUSION IMPLANT AND RELATED METHODS

CROSS-REFERENCE TO RELATED APPLICATION

This application claims the benefit of the filing date under 35 USC 119(e) of provisional application entitled "Spinal Fusion Implant," Ser. No. 60/719,845, filed Sep. 24, 2005, the entire contents of which is fully incorporated herein by reference.

BACKGROUND OF THE INVENTION

I. Field of the Invention

The present invention relates generally to spinal surgery and, more particularly, to a device for spinal fusion comprising a spinal fusion implant of non-bone construction to be introduced into any variety of spinal target sites.

II. Discussion of the Prior Art

Currently there are nearly 500,000 spine lumbar and cervical fusion procedures are performed each year in the United States. One of the causes of back pain and disability results from the rupture or degeneration of one or more intervertebral discs in the spine. Surgical procedures are commonly performed to correct problems with displaced, damaged, or degenerated intervertebral discs due to trauma, disease, or aging. Generally, spinal fusion procedures involve removing some or the all of the diseased or damaged disc, and inserting one or more intervertebral implants into the resulting disc space.

Minimally invasive methods of performing spinal fusion have gained popularity in recent years due to the many benefits of the procedure which include diminished dissection of body tissue and lower blood loss during surgery resulting in reduced surgery time, lower post-operative pain and a quicker recovery for patients. Transforaminal lumbar interbody fusion (TLIF) procedures provide unilateral access to a desired target site. The TLIF technique involves approaching the spine in a similar manner as a posterior approach but more from the left or right of the spine through a midline incision in a patient's back. This procedure requires only one incision in the back of a patient and involves placing a fusion device into the intervertebral disc space. Introducing the intervertebral implant serves to restore the height between adjacent vertebrae ("disc height"), which reduces if not eliminates neural impingement commonly associated with a damaged or diseased disc. Distraction of the disc space with subsequent decompression of nerve roots can be accomplished by rotating a device between the adjacent vertebrae.

Current spinal fusion implants utilize grafts of either bone or artificial implants to fill the intervertebral disc space. Spinal fusion implants or grafts may be made of metal, plastic composites, ceramics, or bone. Natural bone grafts have also been developed including autologous and allograft bone grafts. Other bone grafts may include certain man-made substances including binder joining bone chips and composite bone structures.

While generally effective, the use of bone grafts presents several disadvantages. Autologous bone grafts are obtained from bone material surgically removed from the iliac crest of a patient. This method can be detrimental because it may not yield a sufficient quantity of graft material, requires additional surgery, and increases the risk of infection and blood loss. Moreover, the structural integrity at the donor site can be reduced and significant morbidity associated with harvesting the autologous bone graft may occur.

Allograft bone grafts are obtained from cadaveric specimens, machined, and sterilized for implantation. Production of allograft bone implants may be difficult because of the inherent challenges in forecasting the receipt of cadavers. Allograft may also only provide temporary support as it is difficult to manufacture the allograft with consistent shape and strength given the differing characteristics of cadavers.

A need remains for fusion implants that preserve the intradiscal space and support the vertebral column until the adjacent vertebrae are fused and still encourage bone ingrowth to achieve a solid fusion. A need also remains for implants which maximize anterior surface engagement, better facilitate self distraction during insertion, and allows simple verification of proper position and orientation.

The present invention is directed at overcoming, or at least improving upon, the disadvantages of the prior art.

SUMMARY OF THE INVENTION

The present invention overcomes the drawbacks of the prior art by providing a spinal fusion implant of non-bone construction. The non-bone construction of the spinal fusion implant of the present invention overcomes the drawbacks of the prior art in that it is not supply limited (as with allograft) and does not require harvesting bone from the patient (as with allograft). The present invention better facilitates ring contact and fit between anterior ring portions of vertebral endplates, provides self distraction during insertion and rotation, and avoids dural impingement.

The spinal fusion implant of the present invention may comprise of any suitable non-bone composition, including but not limited to polymer compositions (e.g. poly-ether-ether-ketone (PEEK) and/or poly-ether-ketone-ketone (PEKK)), ceramic, metal, or any combination of these materials. The spinal fusion implant of the present invention may be provided in any number of suitable shapes and sizes depending upon the particular surgical procedure or need. The spinal fusion implant may be dimensioned for use in any region in the spine without departing from the scope of the present invention, such as lumbar fusion surgery via a transforaminal surgical approach to the spine. The implant may be dimensioned, by way of example only, having a width ranging between 8 and 14 mm, a height ranging between 7 and 18 mm, and a length ranging between 25 and 45 mm.

According to one broad aspect of the present invention, the spinal fusion implant includes top and bottom surfaces, first and second side surfaces, and proximal and distal ends. The spinal fusion implant of the present invention may be used to provide temporary or permanent fixation along an orthopedic target site. To do so, the spinal fusion implant may be introduced into a disc space while locked to a surgical insertion tool and thereafter manipulated into the proper orientation before being released. Having been deposited in the disc space, the spinal implant of the present invention effects spinal fusion over time as the natural healing process integrates and binds the implant within the intervertebral space by allowing a honey bridge to form through the implant and between the adjacent vertebral bodies.

The spinal fusion implant of the present invention may be provided with any number of additional features for promoting fusion, such as at least one aperture extending between the top and bottom surfaces to allow a honey bridge to form through the spinal fusion implant. The spinal implant may also be preferably equipped with one or more lateral openings which aid in visualization at the time of implantation and at subsequent clinical evaluations.

Further, the spinal fusion implant may be provided with any number of suitable anti-migration features to prevent the implant from migrating or moving from the disc space after implantation. Suitable anti-migration features may include, but are not necessarily limited to, angled teeth or ridges formed along the top and bottom surfaces of the implant.

The spinal fusion implant may also be provided with image enhancing features to aid in the verification of proper implant positioning and orientation. Suitable image enhancing features may include, but are not necessarily limited to, radiopaque rod elements disposed within the implant.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The spinal fusion implant disclosed herein boasts a variety of inventive features and components that warrant patent protection, both individually and in combination.

Figure 1:
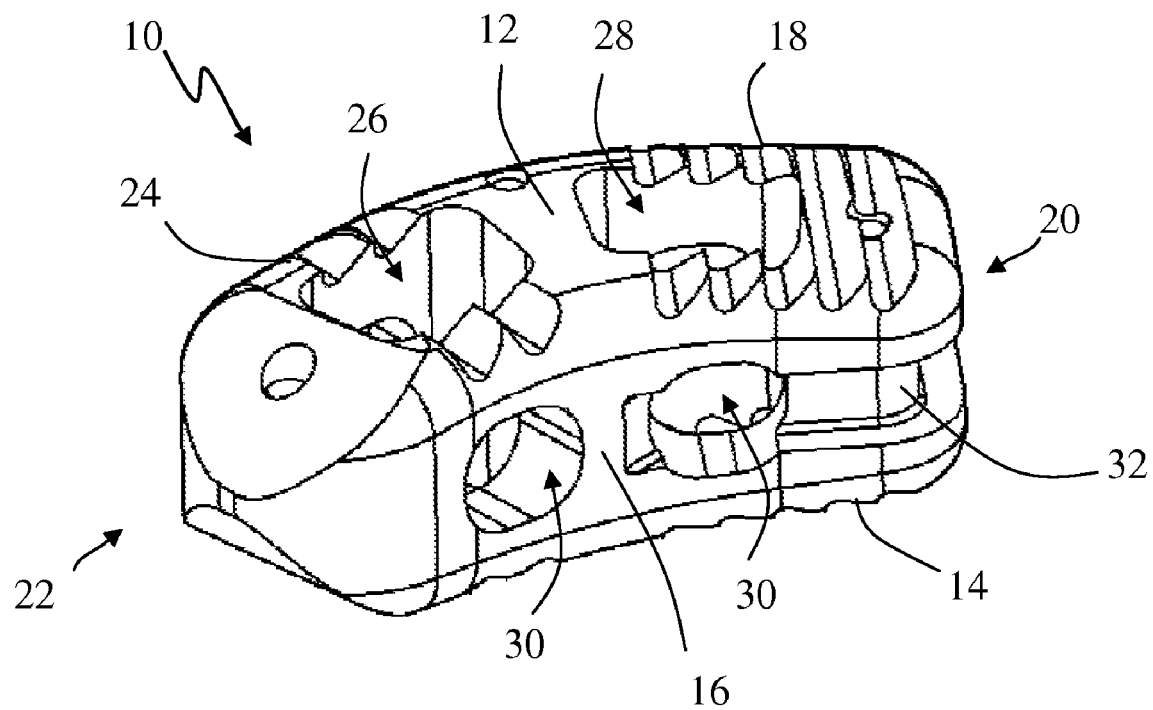
FIG. 1 is a perspective view of a spinal fusion implant illustrating (among other things) multiple fusion apertures extending between top and bottom surfaces, multiple visualization apertures extending through lateral sides, anti-migration features disposed along top and bottom surfaces, an attachment channel along a proximal end, and conical distal end according to one embodiment of the present invention.
Figure 2:
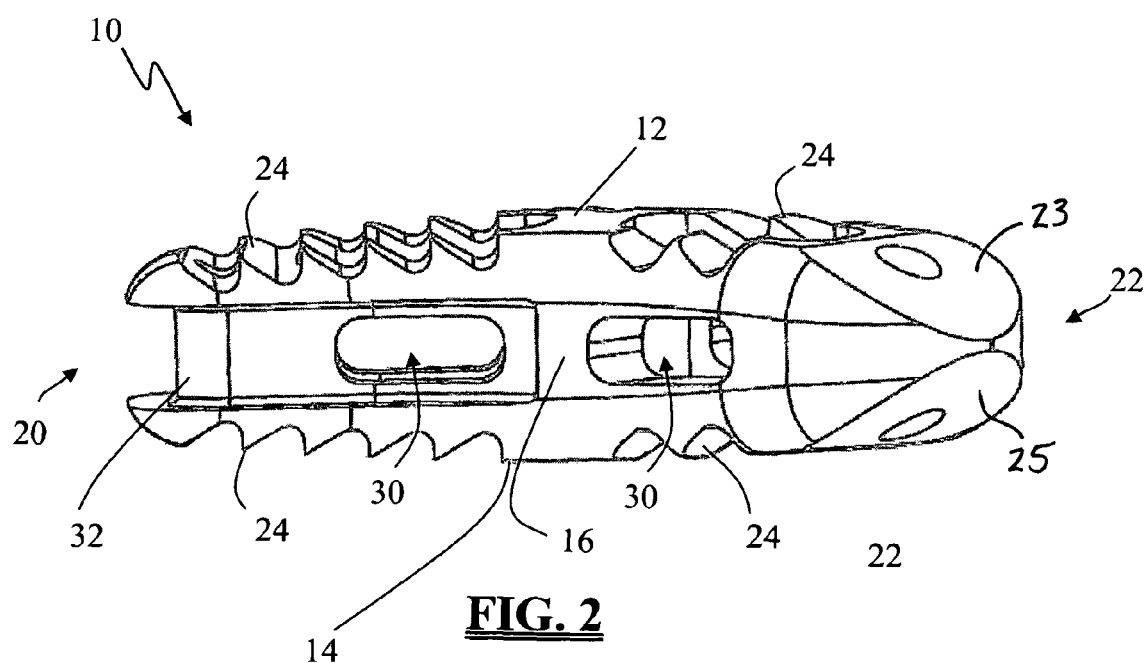
FIG. 2 is a side view detailing a first side surface of the spinal fusion implant of the present invention, illustrating (among other things) multiple visualization apertures, anti-migration features disposed along top and bottom surfaces, an attachment channel along a proximal end, and conical distal end according to one embodiment of the present invention.

FIGS. 1-2 illustrate a spinal fusion implant 10 according to a first broad aspect of the present invention. The spinal fusion implant 10 may be constructed of any suitable non-bone composition having suitable radiolucent characteristics, including but not limited to polymer compositions (e.g. poly-ether-ether-ketone (PEEK) and/or poly-ether-ketone-ketone (PEKK)) or any combination of PEEK and PEKK. The spinal fusion implant 10 of the present invention may be dimensioned, by way of example only, having a width ranging between 8 and 14 mm, a height ranging between 7 and 18 mm, and a length ranging between 20 and 45 mm.

The spinal fusion implant 10 of the present invention includes a top surface 12, a bottom surface 14, a first side surface 16, a second side surface 18, a proximal end 20, and a distal end 22. The spinal fusion implant 10 of the present invention may be used to provide temporary or permanent fixation along an orthopedic target site. To do so, the spinal fusion implant 10 may be introduced into a disc space while locked to a surgical insertion instrument and thereafter manipulated into the proper orientation before being released. To facilitate this, the distal end 22 has a conical (bullet-shaped) shape including two generally angled surfaces 23, 25 which provides gentle self distraction of the disc space during insertion of the spinal fusion implant 10. Having been deposited in the disc space, the spinal fusion implant 10 of the present invention effects spinal fusion over time as the natural healing process integrates and binds the implant within the intervertebral space by allowing a boney bridge to form through the implant and between the adjacent vertebral bodies.

Figure 3:
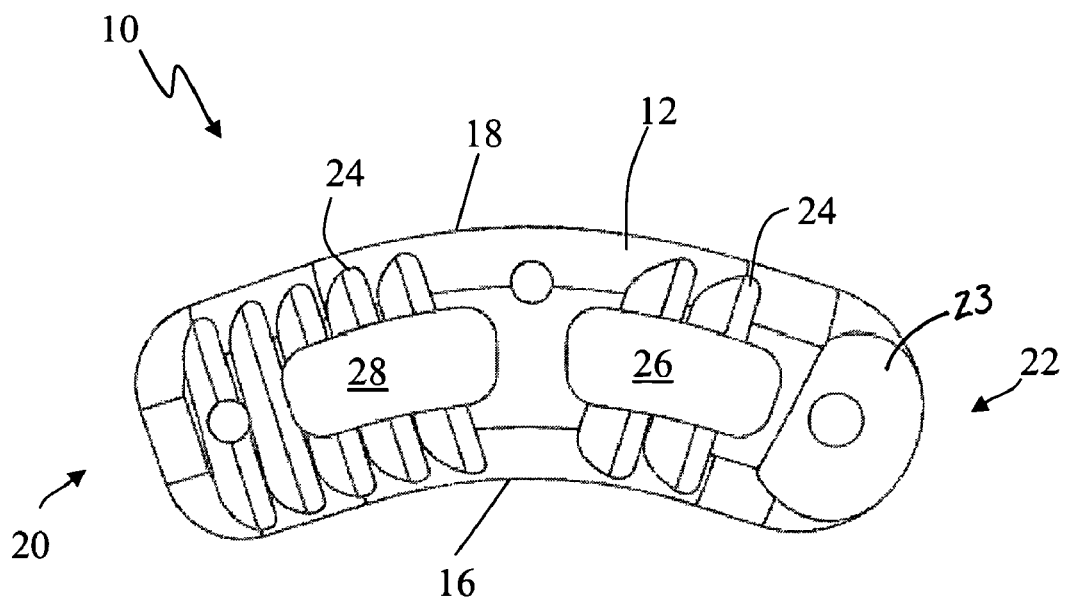
FIG. 3 is a top view of the spinal fusion implant of the present invention, illustrating (among other things) a top surface including multiple fusion apertures, anti-migration features, and image enhancing rod elements according to one embodiment of the present invention.
Figure 4:
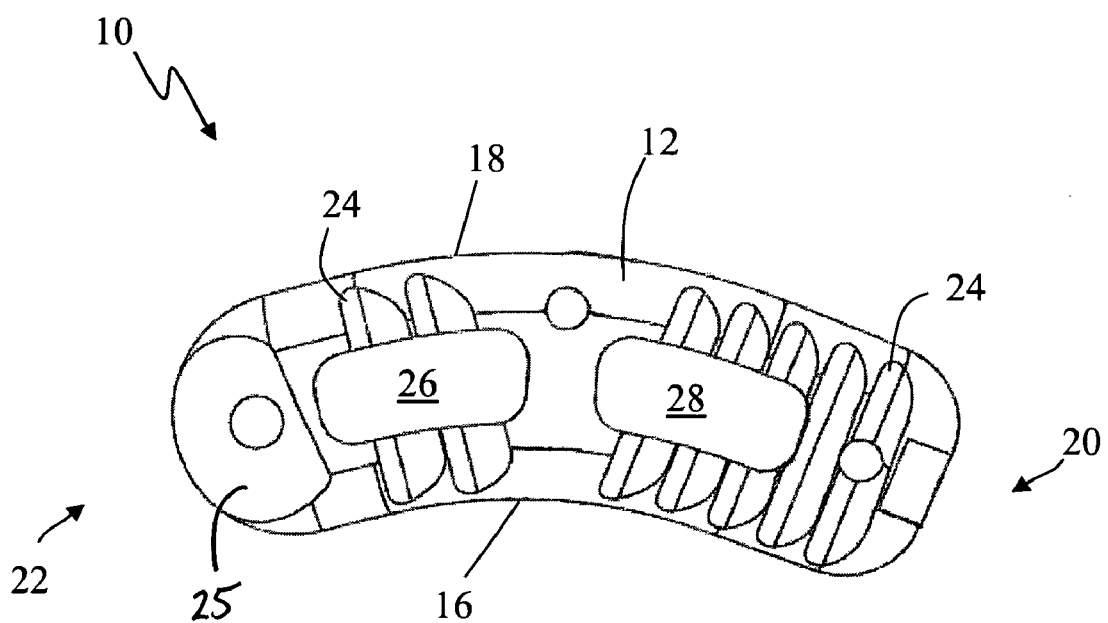
FIG. 4 is a bottom view of the spinal fusion implant of the present invention, illustrating (among other things) a bottom surface including multiple fusion apertures, anti-migration features, and image enhancing rod elements according to one embodiment of the present invention.

FIGS. 3-4 illustrate the top surface 12 and bottom surface 14 according to a first embodiment of the present invention. The top and bottom surfaces 12, 14 are preferably transposable to accommodate insertion of the same implant from either side of the body. This is best illustrated in FIGS. 3-4 wherein FIG. 3 and FIG. 4 represent a single implant 10. In FIG. 3 the implant 10 is positioned such that it may be inserted between adjacent vertebrae utilizing a transforaminal surgical approach from the left side of the patient's mdline. To utilize a transforaminal surgical approach from the right side of the patient's midline, the implant 10 need only be flipped over as illustrated in FIG. 4, wherein bottom surface 14 becomes the top surface and vice versa.

Figure 5:
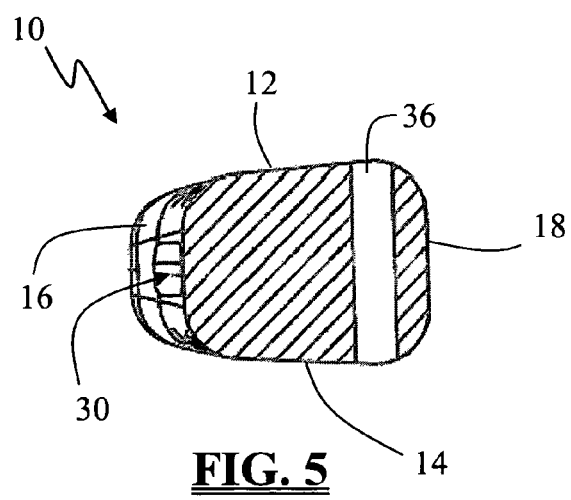
FIG. 5 is a cross-sectional view of the spinal fusion implant of the present invention, illustrating (among other things) the angled relationship between the top and bottom surfaces due to height difference between the first and second side surfaces, and an image enhancing rod element according to one aspect of the present invention.

The top and bottom surfaces 12, 14, as best depicted in FIG. 5, are angled between the first and second side surfaces 16, 18. In lumbar surgical applications, the first side surface 16 will preferably be positioned facing posteriorly within the disc space while the second side surface 18 will preferably be positioned facing anteriorly within the disc space. In this manner, the implant 10 helps maintain the adjacent vertebral bodies in lordosis, which is the natural curvature of the lumbar spine. The height of the first and second side surfaces 16, 18 may be varied such that the angle between the top and bottom surfaces 12, 14 ranges from 3 and 20 degrees, and more preferably from 6 and 15 degrees. It can be appreciated by those skilled in the art that the top and bottom surfaces 12, 14 may be configured in any number of suitable shapes to better match the natural contours of the vertebral end plates.

The top and bottom surfaces 12, 14 preferably include anti-migration features designed to increase the friction between the spinal fusion implant 10 and the adjacent contacting surfaces of the vertebral bodies so as to prohibit migration of the spinal fusion implant 10 after introduction to a desired disc space. Such anti-migration features may include ridges (or teeth) 24 provided along the top surface 12 and/or bottom surface 14. The friction prohibits migration of the implant 10 during the fusion process. It should be appreciated by those skilled in the art that such anti-migration ridges (or teeth) 24 can be oriented in any of a variety of suitable directions in order to stabilize the implant in several degrees of rotation during and/or after placement.

The top and bottom surfaces 12, 14 also include at least one large aperture. A preferred embodiment includes a large distal aperture 26 and a large proximal aperture 28. FIGS. 1, 3-4, & 7 illustrate distal and proximal apertures 26, 28 extending in a vertical fashion between the top and bottom surfaces 12, 14. The apertures 26, 28 may be provided in any of a variety of suitable shapes in addition to the generally rectangular shape best viewed in FIGS. 3-4, including but not limited to generally circular, oblong, and/or triangular shape or any combination thereof. Distal apertures 26 and proximal aperture 28 are additional features for promoting fusion between the upper and lower vertebral bodies which allow a boney bridge to form through the spinal fusion implant 10.

According to another further aspect of the present invention, this fusion may be facilitated or augmented by introducing or positioning various osteoinductive materials within the apertures 26 and 28 and/or adjacent to the spinal fusion implant 10. Such osteoinductive materials may be introduced before, during, or after insertion of the exemplary spinal fusion implant 10, and may include (but are not necessarily limited to) autologous bone harvested from the patient receiving the spinal fusion implant 10, bone allograft, bone xenograft, any number of non-bone implants (e.g. ceramic, metallic, polymer), bone morphogenic protein, and bio-resorbable compositions, including not limited to any of a variety of poly (D, L-lactide-co-glycolide) based polymers, such as disclosed in U.S. Pat. No. 6,013,853.

Figure 6:
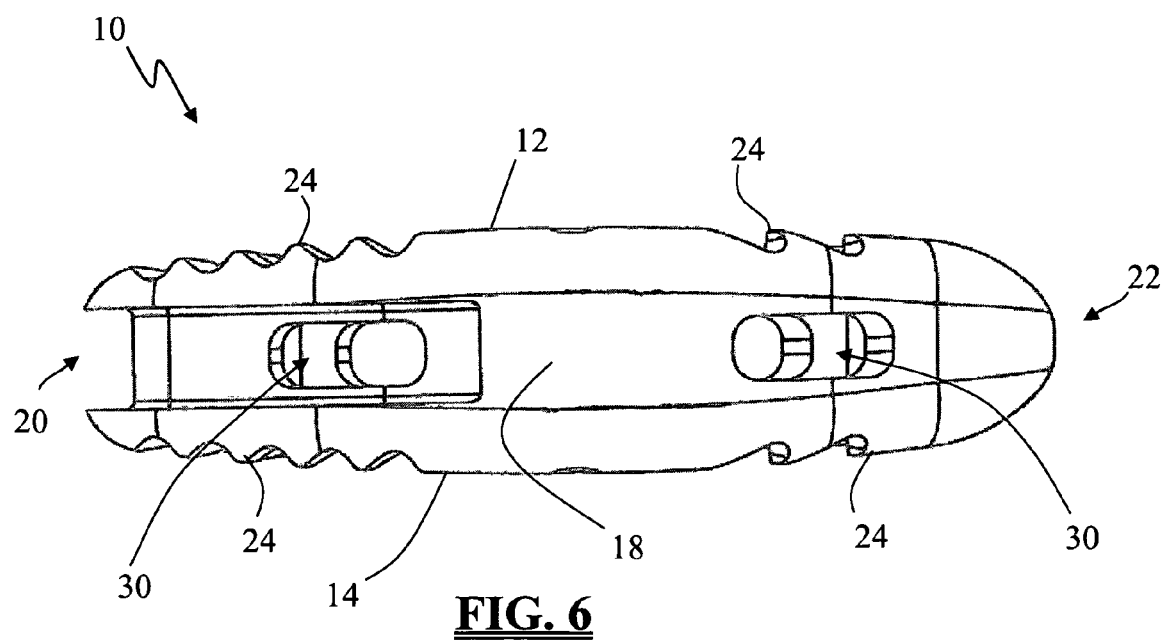
FIG. 6 is a side view of the detailing a second side surface of the spinal fusion implant of the present invention, illustrating (among other things) a lateral visualization opening, an attachment channel, and anti-migration features disposed along top and bottom surfaces according to one embodiment of the present invention.

FIG. 6 illustrates the second side surface 18 according to a first embodiment of the present invention. First and second side surfaces 16 and 18 exhibit a generally curved peripheral shape. The curvature of second side surface 18 mimics the general curvature of the anterior portion of a lumbar disc space allowing for maximum anterior surface engagement with the outer portions of the vertebral anatomy. First side surface 16 and second side surface 18 each include one or more lateral openings 30 which provide visualization (e.g. x-ray or fluoroscopy) at the time of implantation and at subsequent clinical evaluations. These lateral openings 30 extend perpendicularly through the surface of side surfaces 16 and 18. The lateral openings 30 may be provided in any of a variety of suitable shapes in addition to the generally rectangular shape best viewed in FIG. 2, including but not limited to generally circular, oblong, and/or triangular shape or any combination thereof.

More specifically, based on the generally radiolucent nature of the implant 10, the lateral openings 30 provide the ability to visualize the interior of the implant 10 during X-ray and/or other suitable imaging techniques which are undertaken from the lateral (or "side") perspective of the implant 10. If fusion has taken place, the lateral openings 30 will provide a method for the surgeon to make follow up assessments as to the degree of fusion without any visual interference from the spinal fusion implant 10. Further, the lateral openings 30 will provide an avenue for cellular migration to the exterior of the spinal fusion implant 10. Thus the spinal fusion implant 10 will serve as additional scaffolding for bone fusion on the exterior of the spinal fusion implant 10.

Figure 7:
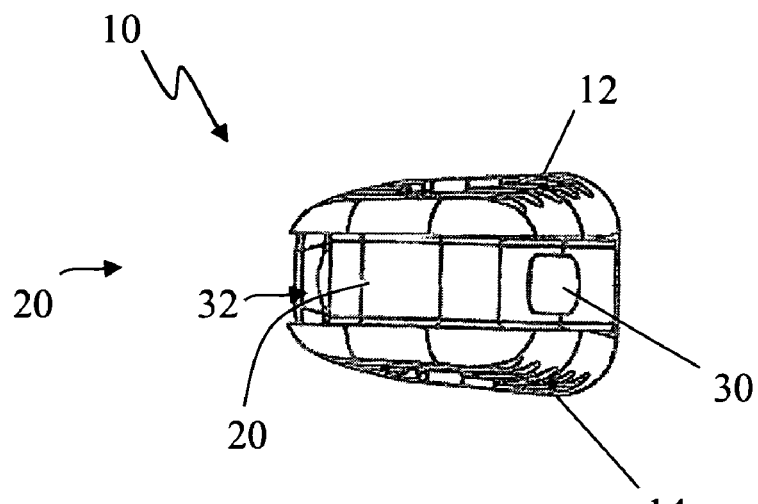
FIG. 7 is a perspective view of the proximal end of the spinal fusion implant of the present invention, illustrating (among other things) a lateral visualization opening and an attachment channel according to one embodiment of the present invention.
Figure 8:
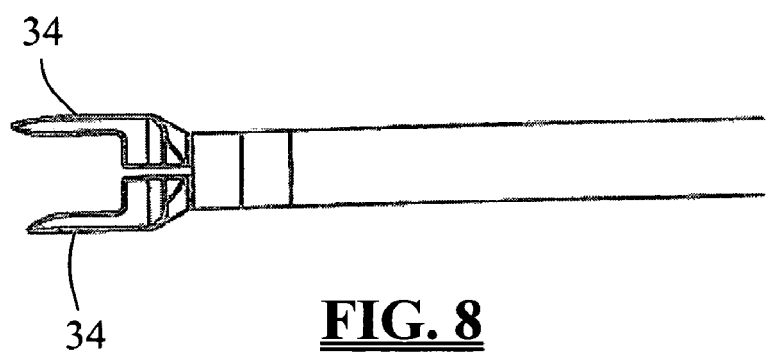
FIG. 8 is a side view of an insertion tool illustrating (among other things) fork-like prongs capable of engaging the attachment channel of the implant of the present invention and releasably attaching the implant.
Figure 9:
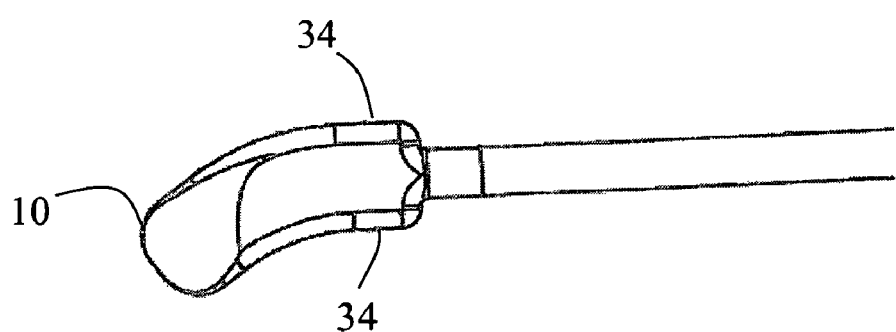
FIG. 9 is a side view of the insertion tool of FIG. 8 releasably attached to the spinal fusion implant of the present invention.

FIG. 7 illustrates the proximal end 20 of the spinal fusion implant 10 of the present invention. In a preferred embodiment proximal end 20 includes a cutout region between the top and bottom surfaces 12, 14 creating an attachment channel 32. Attachment channel 32 extends from proximal end 20 along a portion of the first and second side surfaces 16 and 18, as best viewed in FIG. 2. The attachment channel 32 provides for a preferred method of attaching the spinal fusion implant 10 to an insertion tool such as that shown in FIG. 8. The insertion tool pictured in FIG. 8 includes generally fork-like prongs 34 which slide into the attachment channel 32 formed in the implant 10, after which a compressive force may be applied to the fork-like prongs 34 to squeeze the implant 10 until it becomes releasably attached to the insertion tool as illustrated in FIG. 9. The fusion implant 10 may thereafter be inserted into the desired disc space and properly positioned before removing the compressive force on the fork-like prongs 34, which thereby releases the implant and allows for removal of the insertion tool. Alternatively, various other attachment methods may be utilized, including but not necessarily limited to a threaded aperture (not shown) positioned in proximal end 20.

Figure 10B:
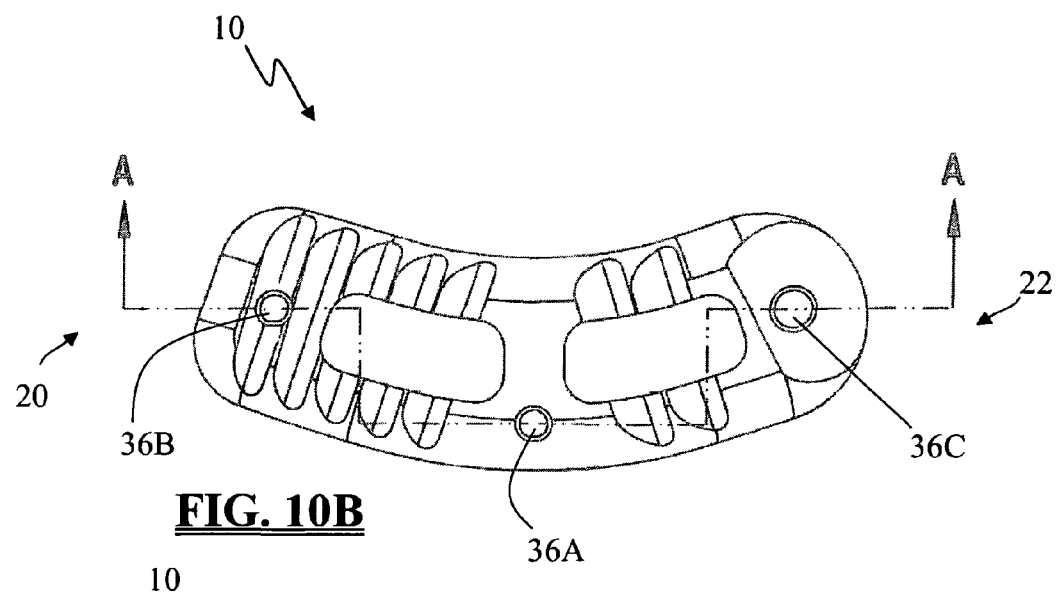
FIG. 10A is a cross-sectional view cut along the line A-A of the spinal fusion implant of FIG. 10B (which a top view of the spinal implant of the present invention), illustrating (among other things) image enhancing rod elements and lateral visualization apertures according to one embodiment of the present invention.
Figure 10A:
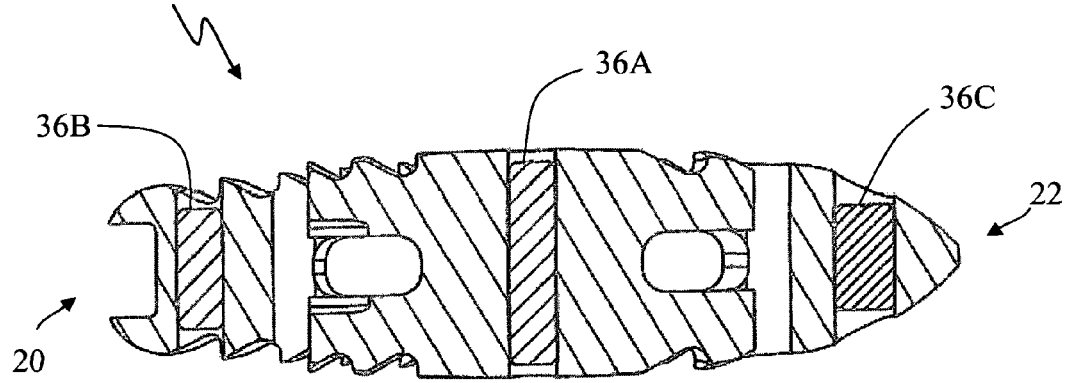

As detailed in FIGS. 10A and 10B, the spinal fusion implant 10 of the present invention preferably includes three rod element 36A, 36B, 36C disposed within the implant to facilitate x-ray or other suitable imaging. A first rod element 36A is positioned approximately midway between proximal and distal ends 20 and 22 adjacent to the second side surface 18. A second rod element 36B is positioned in the proximal end 20 approximately midway between the first and second sides 16 and 18. A third rod element 36C is positioned in the distal end 22 approximately midway between the first and second sides 16 and 18. The rod elements 36A-36C may be manufactured from any of a variety of suitable materials, including but not limited to a metal, ceramic, and/or polymer material, preferably having radiopaque characteristics. The rod elements 36A-36C may also take any of a variety of suitable shapes, including but not limited to a generally elongated cylindrical element disposed within the implant 10 such that the ends thereof extend perpendicularly from approximately the top surface 12 to the bottom surface 14 of the implant 10.

According to one aspect of the present invention, as best shown in FIGS. 10A-10B, the rod elements 36A-36C each have a distinct shape that is different than the others. As will be described below, this is advantageous in that it facilitates the imaging of the spinal implant 10 both intraoperatively and post-operatively to monitor the placement of the spinal implant 10. According to one embodiment, the first rod element 36A and second rod element 36B are the same approximate diameter, while the third rod element 36C has a substantially larger diameter. The heights are each unique, with the first rod element 36A being the longest, the third rod element 36C being the shortest, and the second rod element 36B being in between the height of the first and third rod elements 36A, 36C, respectively.

Figure 11:
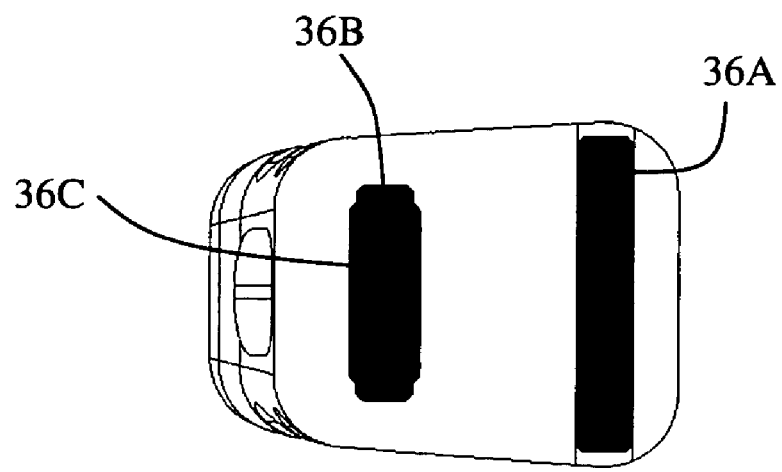
FIG. 11 is a simulated lateral image (e.g. x-ray or fluoroscopy) of the spinal fusion implant of the present invention, illustrating (among other things) the varying sizes of image enhancing rod elements and the proper alignment of rod elements when the implant is properly positioned in the disc space.
Figure 12:
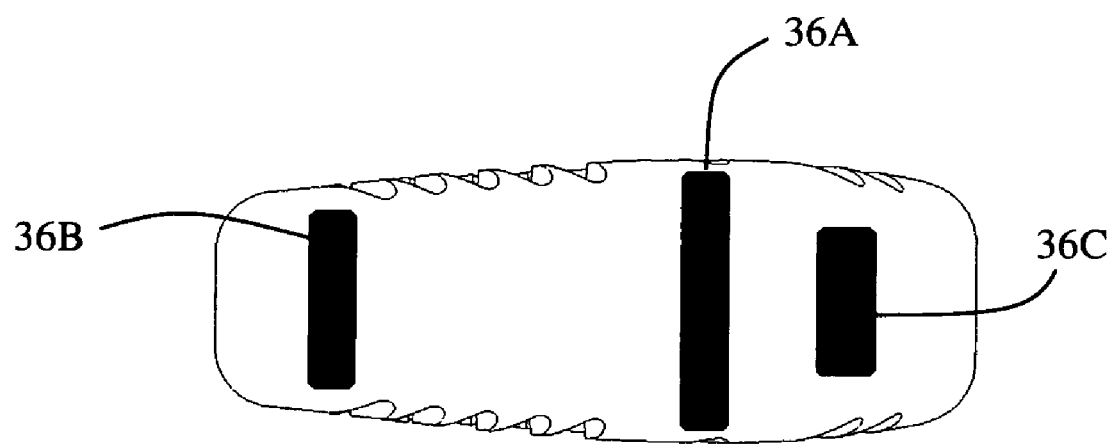
FIG. 12 is a simulated lateral x-ray image of the spinal fusion implant of the present invention, illustrating (among other things) the varying sizes of image enhancing rod elements and the offset alignment of rod elements when the implant is not yet properly positioned in the disc space.

The individual sizing of rod elements 36A-36C allows them to be individually distinguished during imaging. This is best appreciated in FIGS. 11 and 12, which show a representation of implant 10 after implantation in the body as if shown using X-ray or other suitable imaging technique. The relative placement of rod elements 36A-36C, described above, permits simple verification of the proper placement and orientation of the implant 10 within the disc space. Utilizing X-ray and/or other suitable imaging techniques from the lateral (or "side") perspective of the patient, the rod elements 36A-36C situated in the proximal and distal ends 20 and 22 will align when the implant is properly positioned with the second side surface 18 located along the anterior region of the disc space, as depicted in FIG. 11. Conversely, using the same lateral imaging, the rod elements 36A-36C will appear offset as depicted in FIG. 12 during introduction of the spinal implant 10 or if the spinal implant 10 is not in the proper position (with the second side surface 18 located along the anterior region of the disc space).

According to a broad aspect of the present invention, the spinal fusion implant 10 may be introduced into a spinal target site through use of any of a variety of suitable surgical instruments having the capability to engage the spinal implant. A clinician may utilize the implant 10 in a minimally invasive spinal fusion procedure. After creation of a working channel and preparation of the disc space, a single oblique fusion device is placed into the intervertebral disc space. Additional materials and tools may be included in the procedure before, during, or after the insertion of the implant 10 to aid in introducing the implant into a targeted spinal site.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined herein.

What is claimed is:

1. A spinal fusion implant, comprising:
 a body composed of non-bone, radiolucent material having a top surface having a plurality of anti-migration features, a bottom surface having a plurality of anti-migration features, a first curved side surface extending between the top and bottom surfaces, a second curved side surface extending between the top and bottom surfaces opposite from the first curved side surface and having a height greater than the first side surface, at least one fusion aperture extending between the top and bottom surfaces of the body, said body including an attachment feature releasably coupleable to an insertion tool said body including a first radiopaque image enhancing element approximate to the apex of the curve of the second side surface, a second radiopaque image enhancing element disposed approximate to the proximal end of the body, and a third radiopaque image enhancing element disposed approximate to the distal end of the body to facilitate proper positioning of the body within a disc space, wherein said first radiopaque element and said second radiopaque element are generally cylindrical with the same approximate diameter but different heights, and wherein the third radiopaque element is generally cylindrical with a diameter larger than the diameter of the first and second radiopaque elements and a height smaller than said first and second radiopaque elements.

2. The spinal fusion implant of claim 1, wherein said body is composed of at least one of a polymer composition, ceramic, and a combination of polymer, ceramic and metal.

3. The spinal fusion implant of claim 1, wherein the width of said top and bottom surfaces of said body is between 8 mm and 14 mm.

4. The spinal fusion implant of claim 1, wherein the height of said first and second side surfaces of said body is between 7 mm and 18 mm.

5. The spinal fusion implant of claim 1, wherein the length of said top and bottom surfaces of said body is between 25 mm and 45 mm.

6. The spinal fusion implant of claim 1, comprising at least one viewing aperture extending between the first and second side surfaces.

7. The spinal fusion implant of claim 1, wherein said plurality of anti-migration elements includes at least one of angled teeth or ridges.

8. The spinal fusion implant of claim 1, wherein said first, second and third radiopaque elements are metallic rods disposed in apertures extending between the top surface and the bottom surface.

9. The spinal fusion implant of claim 1, wherein the second curved side has a height greater than the first curved side such that there is an angle between the top and bottom surfaces between 6 and 15 degrees.

10. The spinal fusion implant of claim 1, further comprising an osteoinductive material positioned at least one of within said at least one fusion aperture and adjacent to said body.

11. The spinal fusion implant of claim 10, wherein said osteoinductive material includes at least one of autologous bone, bone allograft, bone xenograft, a non-bone implant, a bone morphogenic protein and a bio-resorbable composition.

12. The spinal fusion implant of claim 1, wherein said implant has a wedged distal end.

13. The spinal fusion implant of claim 12, wherein said wedged distal end includes a first wedge surface and a second wedge surface that converge to facilitate insertion of said implant into said disc space.

14. The spinal fusion implant of claim 1, wherein said attachment feature is a channel extending along the length of said proximal end and along a portion of each of said first and second curved sides.

15. The spinal fusion implant of claim 1, wherein said body includes a a first fusion aperture extending between the top and bottom surfaces adjacent the proximal end of the body and a second fusion aperture extending between the top and bottom surfaces adjacent the distal end of the body.

16. A system for performing spinal fusion surgery, comprising:
- an implant composed of non-bone, radiolucent material having a top surface having a plurality of anti-migration features, a bottom surface having a plurality of anti-migration features, a first curved side surface extending between the top and bottom surfaces, a second curved side surface extending between the top and bottom surfaces opposite from the first curved side surface and having a height greater than the first side surface, a first at least one fusion aperture extending between the top and bottom surfaces, said implant including an attachment channel extending along the length of said proximal end and along a portion of each of said first and second curved sides, said attachment channel being releasably coupleable to an insertion tool, said implant having radioopaque image enhancing element to facilitate the proper positioning of the implant within a disc space; and a first radiopaque image enhancing element approximate to the apex of the curve of the second side surface, a second radiopaque image enhancing element disposed approximate to the proximal end of the implant, and a third radiopaque image enhancing element disposed approximate to the distal end of the implant to facilitate proper positioning of the implant within a disc space, wherein said first radiopaque element and said second radiopaque element are generally cylindrical with the same approximate diameter but different heights, and wherein the third radiopaque element is generally cylindrical with a diameter larger than the diameter of the first and second radiopaque elements and a height smaller than said first and second radiopaque elements; and
- an insertion tool having a proximal end and a distal end, wherein said distal end includes generally fork-like prongs dimensioned to be releasably coupled to the attachment channel.

17. The system of claim 16, wherein said spinal implant is composed of at least one of a polymer composition, ceramic, and a combination of polymer, ceramic and metal.

18. The system of claim 16, wherein the width of said top and bottom surfaces of said implant is between 8 mm and 14 mm.

19. The system of claim 16, wherein the height of said first and second side surfaces of said implant is between 7 mm and 18 mm.

20. The system of claim 16, wherein the length of said top and bottom surfaces of said implant is between 25 mm and 45 mm.

21. The system of claim 16, comprising at least one viewing aperture extending between the first and second side surfaces.

22. The system of claim 16, wherein said plurality of anti-migration elements includes at least one of angled teeth or ridges.

23. The system of claim 16, wherein said first, second and third radiopaque elements are metallic rods disposed in apertures extending between the top surface and the bottom surface.

24. The system of claim 16, wherein the second curved side has a height greater than the first curved side such that there is an angle between the top and bottom surfaces between 6 and 15 degrees.

25. The system of claim 16, further comprising an osteoinductive material positioned at least one of within said at least one fusion aperture and adjacent to said implant.

26. The system of claim 25, wherein said osteoinductive material includes at least one of autologous bone, bone allograft, bone xenograft, a non-bone implant, a bone morphogenic protein and a bio-resorbable composition.

27. The system of claim 16, wherein said body has a wedged distal end.

28. The system of claim 27, wherein said wedged distal end includes a first wedge surface and a second wedge surface that converge to facilitate insertion of said body into said disc space.

29. The system of claim 16, wherein said body includes a first fusion aperture extending between the top and bottom surfaces adjacent the proximal end of the body and a second fusion aperture extending between the top and bottom surfaces adjacent the distal end of the body.

30. A method of performing spinal fusion surgery, comprising the steps of:
(a) coupling a non-bone spinal implant to an insertion tool, said spinal implant comprising a body composed of non-bone, radiolucent material having a top surface having a plurality of anti-migration features, a bottom surface having a plurality of anti-migration features, a first curved side surface extending between the top and bottom surfaces, a second curved side surface extending between the top and bottom surfaces opposite from the first curved side surface and having a height greater than the first side surface, at least one fusion aperture extending between the top and bottom surfaces, said body including an attachment feature for coupling to said insertion tool, said implant having a first radiopaque image enhancing element approximate to the apex of the curve of the second side surface, a second radiopaque image enhancing element disposed approximate to the proximal end of the body, and a third radiopaque image enhancing element disposed approximate to the distal end of the body to facilitate proper positioning of the body within a disc space, wherein said first radiopaque element and said second radiopaque element are generally cylindrical with the same approximate diameter but different heights, and wherein the third radiopaque element is generally cylindrical with a diameter larger than the diameter of the first and second radiopaque elements and a height smaller than said first and second radiopaque elements;
(b) introducing the spinal fusion implant, using the insertion tool, into a disc space in the lumbar spine via a transforaminal surgical technique; and
(c) positioning the spinal fusion implant within the disc space such that the second side surface is generally adjacent to the anterior region of the disc space.

31. The method of claim 30, wherein said spinal implant is composed of at least one of a polymer composition, ceramic, and a combination of polymer, ceramic and metal.

32. The method of claim 30, wherein the width of said top and bottom surfaces of said implant is between 8 mm and 14 mm.

33. The method of claim 30, wherein the height of said first and second side surfaces of said implant is between 7 mm and 18 mm.

34. The method of claim 30, wherein the length of said top and bottom surfaces of said implant is between 25 mm and 45 mm.

35. The method of claim 30, comprising at least one viewing aperture extending between the first and second side surfaces.

36. The method of claim 30, wherein said plurality of anti-migration elements includes at least one of angled teeth or ridges.

37. The method of claim 30, wherein said first, second and third radiopaque elements are metallic rods disposed in apertures extending between the top surface and the bottom surface.

38. The method of claim 30, wherein the second curved side has a height greater than the first curved side such that there is an angle between the top and bottom surfaces is between 6 and 15 degrees.

39. The method of claim 30, further comprising an osteoinductive material positioned at least one of within said at least one fusion aperture and adjacent to said implant.

40. The method of claim 39, wherein said osteoinductive material includes at least one of autologous bone, bone allograft, bone xenograft, a non-bone implant, a bone morphogenic protein and a bio-resorbable composition.

41. The method of claim 30, wherein said implant has a wedged distal end.

42. The method of claim 41, wherein said wedged distal end includes a first wedge surface and a second wedge surface that converge to facilitate insertion of said implant into said disc space.

43. The method of claim 30, wherein said attachment feature is a channel extending along the length of said proximal end and along a portion of each of said first and second curved sides.

44. The method of claim 30, wherein said body includes a first fusion aperture extending between the top and bottom surfaces adjacent the proximal end of the body and a second fusion aperture extending between the top and bottom surfaces adjacent the distal end of the body.

* * * * *